United States Patent [19]

Coyle

[11] Patent Number: 4,554,054
[45] Date of Patent: Nov. 19, 1985

[54] METHACRYLIC ACID SEPARATION

[75] Inventor: Robert W. Coyle, Horsham, Pa.

[73] Assignee: Rohm and Haas Company, Philadelphia, Pa.

[21] Appl. No.: 560,084

[22] Filed: Dec. 9, 1983

[51] Int. Cl.[4] .......................... B01D 3/36; B01D 11/04
[52] U.S. Cl. ....................................... 203/15; 203/43; 203/73; 203/80; 203/87; 562/600
[58] Field of Search ............. 203/14, 15, 43, DIG. 21, 203/87, 91, 80, 73, 60, 69, DIG. 25, 45, 461; 562/599, 600

[56] References Cited

U.S. PATENT DOCUMENTS

| | | | |
|---|---|---|---|
| 3,344,178 | 9/1967 | Brown et al. | 203/15 |
| 3,405,172 | 8/1968 | Brown et al. | 562/600 |
| 3,414,485 | 12/1968 | Speed | 203/43 |
| 3,493,471 | 2/1970 | Bashaw | 562/600 |
| 3,666,632 | 5/1972 | Honda et al. | 203/DIG. 21 |
| 3,798,264 | 3/1974 | Kubota et al. | 562/600 |
| 3,809,645 | 5/1974 | Matsuzawa et al. | 562/600 |
| 4,142,058 | 2/1979 | Matsumara et al. | 562/600 |
| 4,147,721 | 4/1979 | Leacock | 203/87 |
| 4,234,519 | 11/1980 | Yeoman et al. | 568/492 |

FOREIGN PATENT DOCUMENTS

| | | |
|---|---|---|
| 2164767 | 7/1972 | Fed. Rep. of Germany ...... 562/600 |
| 2161525 | 6/1973 | Fed. Rep. of Germany . |
| 2832202 | 2/1979 | Fed. Rep. of Germany ... 203/DIG. 21 |
| 1008213 | 1/1976 | Japan ................................. 562/600 |
| 56-110642 | 9/1981 | Japan . |
| 2045795A | 11/1980 | United Kingdom . |
| 2004886A | 3/1982 | United Kingdom . |
| 2045759 | 7/1983 | United Kingdom . |

Primary Examiner—Kenneth M. Schor
Assistant Examiner—Virginia Manoharan
Attorney, Agent, or Firm—Terence P. Strobaugh

[57] ABSTRACT

A process to recover acrylic acid or methacrylic acid by using a split quench process which allows acrylic acid or methacrylic acid to be recovered from the resulting aqueous solutions by a combination of solvent extraction and azeotropic dehydration that minimizes the amount of solvent required.

5 Claims, 1 Drawing Figure

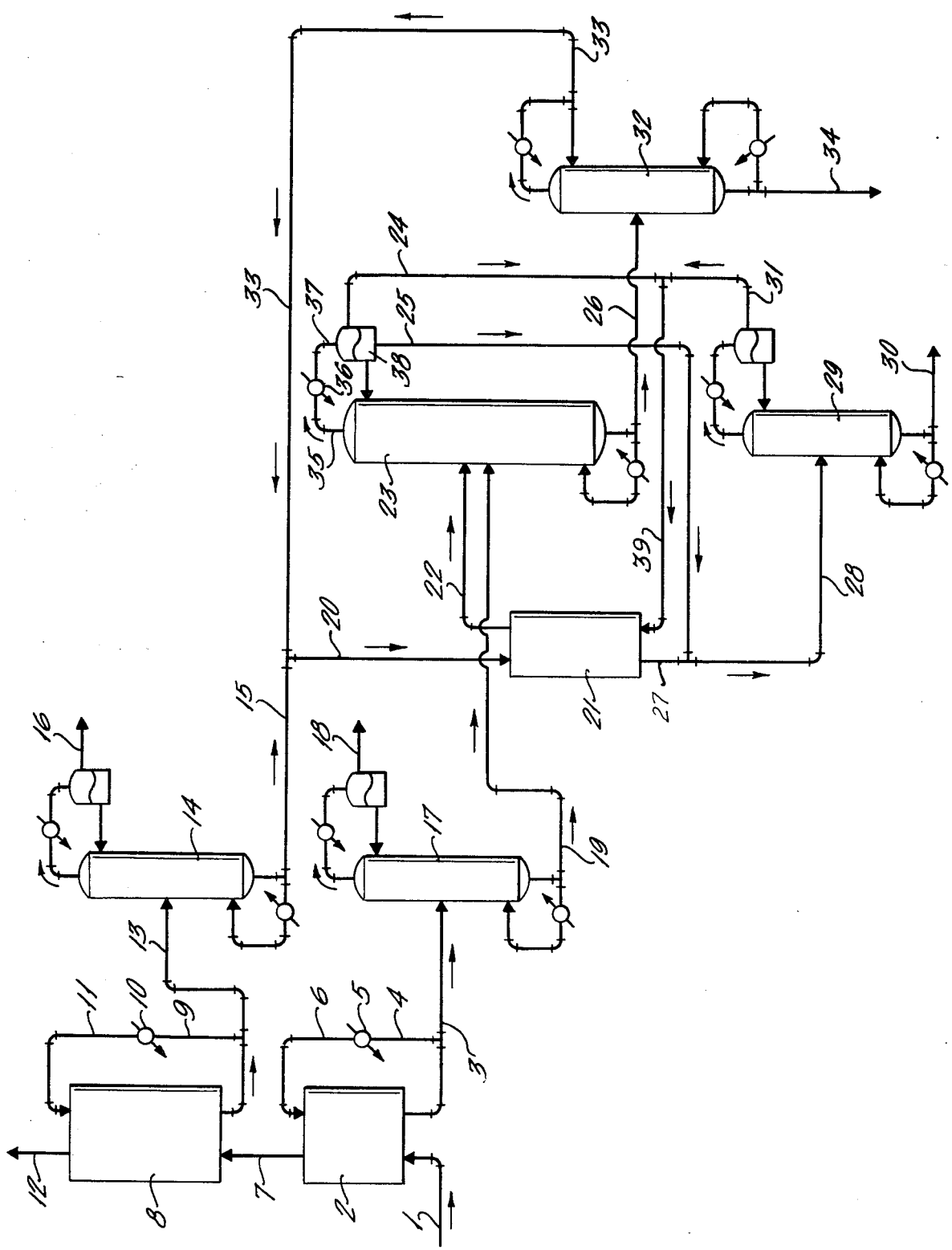

METHACRYLIC ACID SEPARATION

This invention relates to a process for the separation of acrylic acid or methacrylic acid from a gaseous mixture.

When methacrolein (or a precursor) is oxidized in the gas phase with water vapor and molecular oxygen (usually air) in the presence of an oxidation catalyst, a gaseous reaction mixture containing methacrylic acid, acetic acid, water, carbon monoxide, carbon dioxide, unreacted methacrolein (or the precursor), oxygen, and nitrogen is obtained. Methacrylic acid is only a small portion of the effluent stream, because substantial quantities of steam and inert gases are used in the process. The methacrylic acid must be separated from the water; however, this separation is difficult because methacrylic acid forms an azeotrope with water.

A precursor is any compound which under suitable reaction conditions yields the compound to be employed (e.g. catalytic oxidation). Precursors of methacrolein include isobutylene, tert-butanol or tert-butyl alkanoates.

RELATED ART

GB No. 2,045,759 A is directed to a process for the recovery of methacrylic acid from an aqueous solution. It discloses that the gaseous effluent is cooled and condensed by direct contact with recirculating condensed effluent. A portion of the recirculating effluent is withdrawn and fed to an extraction column where methacrylic acid is separated from the aqueous solution with an organic solvent. To obtain essentially complete recovery of methacrylic acid from the effluent, the recirculating liquid stream must be cooled. Since water in the reactor effluent is condensed along with methacrylic acid, the liquid leaving the reactor effluent condenser is relatively dilute in methacrylic acid. Cooling the gas stream fed to the condenser to 40 C., results in a concentration of the liquid condenser effluent of not more than 42 weight percent methacrylic acid.

Methacrolein is recovered from the vapor phase effluent of the condenser by absorption. An example of this recovery is disclosed in U.K. Patent GB No. 2,004,886 A. In the absorption-separation of methacrolein and methacrylic acid from the gaseous reaction mixture by this process, most of the methacrylic acid is recovered from the vapor phase in the condenser(s) and/or methacrolein absorber, along with a substantial portion of the water vapor contained in the reaction mixture. The aqueous stream from which methacrylic acid is recovered is relatively dilute which makes the isolation of methacrylic acid difficult.

The following processes have been developed for the recovery of methacrylic acid from an aqueous solution by extraction with an organic solvent. In U.K. patent application No. 2,045,795A, a mixture of methyl n-propyl ketone and toluene is used to separate methacrylic acid from water and reaction by-products. U.S. Pat. No. 3,414,485 discloses a process where methacrylic acid is recovered by extraction with xylene, methyl methacrylate, toluene, octane, chlorobenzene, methylamyl ketone or ligroin. In Ger. Offen. No. 2,161,525, methacrylic acid is recovered by extraction with a mixture of methylethyl ketone and hexane. Japan Kokai No. 81–79634 discloses the recovery of methacrylic acid by extraction with hexane, while Japan Kokai No. 73–39,421 refers to a process where methacrylic acid is recovered by extraction with a mixture of methylethyl ketone and di-isobutylene. U.S. Pat. No. 3,809,645 discloses recovery of methacrylic acid by extraction with a mixture of methyl methacrylate and methanol. Methanol transfers from the organic phase to the aqueous phase and methacrylic acid transfers from the aqueous phase to the organic phase. In Japanese Patent Application No. 81-110642 methacrylic acid is recovered by extraction with a mixture of ethyl benzene and xylene. See also U.S. Pat. Nos. 4,234,519 and 4,142,058.

Solvent extraction is favored because methacrylic acid forms a low-boiling azeotrope with water that prevents the separation of methacrylic acid and water by simple distillation. However, since large quantities of solvent are required to recover high yields of methacrylic acid, the subsequent separation of solvent from methacrylic acid requires large amounts of steam, (i.e. energy) making these processes commercially unsuitable.

SUMMARY OF THE INVENTION

This invention involves a "split quench" scheme whereby the effluent from the methacrolein oxidation reactor is quenched in two steps to provide a concentrated aqueous methacrylic acid stream and a dilute aqueous methacrylic acid stream. Unreacted methacrolein contained in the non-condensibles from the first quenching step can be recovered along with methacrylic acid in the second quench step or can be recovered separately. The dilute stream from the second quench step is fed directly to a solvent extractor where methacrylic acid is recovered from the aqueous phase by extraction with a solvent that forms a low-boiling azeotrope with water. The organic phase from the extractor and the concentrated methacrylic acid stream from the first quench are fed to a distillation column where the solvent/water azeotrope is removed overhead. This process has lower capacity requirements for the extraction and distillation steps than presently known processes.

This invention provides a process for separating methacrylic acid from reactor effluent gases obtained from the gas phase catalytic oxidation of methacrolein or a methacrolein precursor.

In general, the process comprises:

(a) feeding the gaseous reactor effluent to a first-stage partial condenser wherein the reaction mixture is brought into direct contact with a part of the condensed liquid previously obtained in the condenser, at a temperature in the range of from 16° to 70° C., whereby a portion of the methacrylic acid and water vapor in the reactor effluent are condensed to form a relatively concentrated aqueous methacrylic acid solution and whereby a substantial portion of the methacrylic acid and water vapor leaves the first-stage condenser in the vapor phase along with non-condensible gases and the major portion of the methacrolein contained in the reactor effluent;

(b) feeding the vapor phase, leaving the first-stage condenser, to a second-stage condenser where the vapor is brought into direct contact with a part of the condensed liquid (obtained in the second-stage condenser) at a temperature equal to or less than that of the first-stage condenser whereby most of the methacrylic acid and a large portion of the water contained in the vapor feed are condensed to form an aqueous methacrylic acid solution that is less concentrated in methacrylic acid than the liquid leaving the first-stage condenser:

(c) feeding the liquid stream from the first-stage condenser to a distillation column where methacrolein is removed as an overhead product;

(d) feeding the liquid stream from the second-stage condenser to a second distillation column where methacrolein is removed as an overhead product;

(e) extracting the stream from the bottom of the methacrolein removal column, described in step d, with a suitable solvent; and (f) feeding both the organic phase from the extractor and the liquid from the bottom of the methacrolein removal column, described in step c to a distillation column wherein solvent and water are removed overhead and methacrylic acid is removed from bottom of the column.

The preferred temperature of the effluent gases from the first-stage partial condensation is in the range of from 16° to 70° C.

Preferably, the methacrylic acid, water vapor and methacrolein remaining in the vapor phase effluent (from the first-stage condenser) are fed to a second-stage condenser where up to 99.9% of the methacrylic acid remaining in the vapor phase is condensed by countercurrent contact with a suitable solvent such as water, or recirculated condensate. Preferably, the condensation is by counter-current contact with a recirculating liquid stream cooled to a temperature less than the temperature of the recirculating liquid stream of the first-stage condender. A substantial portion of the water vapor present in the feed to the second-stage condenser is condensed to form an aqueous solution less concentrated in methacrylic acid than the liquid leaving the first-stage condensor.

In a preferred embodiment of this invention, the methacrolein oxidation reactor is operated so that conversion of methacrolein is low to maintain high selectivity to methacrylic acid, and unreacted methacrolein in the vapor phase effluent of the second-stage condenser is recovered for recycle to the methacrolein oxidation reactor. Preferably, both the concentrated methacrylic acid solution leaving the first-stage condenser and the dilute methacrylic acid stream leaving the second-stage condenser are fed to preliminary distillation columns operated at atmospheric pressure or sub-atmospheric pressure at a bottoms temperature in the range of from about 70° to about 150° C. to remove the small amount of dissolved methacrolein and other very-low boiling impurities as overheads. The bottoms stream leaving the preliminary distillation column is sent to a countercurrent extractor where methacrylic acid is removed from the aqueous phase with a suitable solvent.

A suitable solvent is one which:

1. forms an azeotrope with water that boils at a temperature not less than 5° C. lower than the methacrylic acid-water azeotrope boiling point (which at atmospheric is 99° C.),
2. is only partially miscible in water,
3. has a distribution coefficient with methacrylic acid in the range of from about 4 to about 9, and
4. forms an azeotrope with water of not less than 5 weight percent and not more than 40 weight percent water.

Examples of suitable solvents are iso-butyl acetate, sec-butyl acetate, iso-propyl acetate, n-propyl acetate, toluene xylene, methyl methacrylate, ethyl propionate and methyl isobutyrate. The stream from the bottom of the distillation column (which strips methacrolein from the concentrated first-stage condenser effluent) and the organic phase leaving the solvent extractor (which contains most of the methacrylic acid fed to the extractor), are both fed to a distillation column where solvent and water are separated from methacrylic acid. The solvent forms an azeotrope with water in the distillation column, allowing methacrylic acid to be separated from water despite the fact that methacrylic acid and water form a minimum-boiling azeotrope.

The advantage of this invention is that only enough solvent is used in the extractor to completely remove all of the water in the subsequent distillation step as the solvent/water azeotrope. The invention, therefore, substantially reduces the amount of solvent necessary and the energy required to isolate methacrylic acid from aqueous solution.

In an alternative embodiment of the invention, the reactor effluent gases are fed to a first-stage condenser where methacrylic acid and water vapor are partially removed from the vapor phase as in the preferred embodiment described above to form a liquid stream concentrated in methacrylic acid. The remaining methacrylic acid, water vapor and methacrolein, leaving the condenser in the vapor phase, are fed to an absorber at a temperature below 90° C., preferably about 50° C. where methacrolein and methacrylic acid are recovered from the vapor phase by direct contact with a recycled stream of absorber bottoms liquid that has been stripped of methacrolein. Methacrolein is removed from the liquid leaving the absorber by distillation and recycled to the methacrolein oxidation reactor. A portion of the stripped absorber bottoms is fed to the absorber to act as the absorption solvent, while the remainder is sent to an extractor where methacrylic acid is removed from the aqueous phase by solvent extraction, as in the preferred embodiment. The concentrated methacrylic acid solution leaving the condenser is stripped of methacrolein in a distillation column. The stripped methacrylic acid solution and the organic phase leaving the solvent extractor, which contains most of the methacrylic acid fed to the extractor, is fed to a distillation column where solvent and water are separated from methacrylic acid.

Any method may be used to bring liquid and vapor into direct contact in the first- and second-stage condensers, the methacrolein stripping distillation columns or the solvent removal distillation column. Similarly, any type of liquid-liquid contacting device may be used in the solvent extraction step of the process.

BRIEF DESCRIPTION OF THE DRAWINGS

The process of the invention is illustrated in FIG. 1. FIG. 1 shows one embodiment of the apparatus employed to separate methacrylic acid from a gaseous reactor effluent mixture.

DETAILED DESCRIPTION OF THE PREFERRED EMBODIMENTS

Referring to FIG. 1, gaseous effluent from the catalytic oxidation of methacrolein is supplied through line 1 to the first condenser 2. The gas is there brought into contact with a methacrylic acid-containing liquid recycled through a line 4, a cooler 5, and a line 6, whereby a portion of the methacrylic acid and water vapor contained in the mixed gas are condensed. The vapor leaving the first condenser 2 is supplied through a line 7 to a second-stage condenser 8 preferably operated at a temperature lower than that of the first-stage condenser where the gas is brought into contact with a second stream of methacrylic acid-containing liquid recycled through a line 9, a cooler 10, and a line 11, whereby most of the methacrylic acid and water vapor in the mixed gas are condensed. The aqueous methacrylic acid solution leaving the second-stage condenser 8 through line 13 is less concentrated in methacrylic acid than the solution leaving the first-stage condenser 2 through line 3. Preferably, the effluent gas leaving the second condenser 8 through line 12 is treated to recover methacrolein for recycle to the methacrolein oxidation reactor. The methacrylic acid-containing liquid from the bottom of the first condenser 2 is supplied through a line 3 to a preliminary distillation column 17 where methacrolein and other volatile by-products are removed overhead through a line 18. The methacrylic acid-containing liquid from which methacrolein has been stripped in column 17 is removed from the bottom of column 17 through a line 19. The methacrylic acid-containing liquid from the bottom of the second condenser 8 is similarly supplied through a line 13 to another preliminary distillation column 14 where methacrolein and other light by-products are removed overhead through line 16 and where the methacrylic acid-containing liquid which has been stripped of methacrolein is removed from the bottom of the column through a line 15. The liquid leaving the bottom of the second distillation column 14 through line 15 is fed through line 20 to a solvent extractor 21 where the feed liquid is brought into counter-current contact with solvent supplied through line 39. The organic phase leaving the extractor through line 22 contains most of the methacrylic acid fed to the extractor and is sent with the concentrated methacrylic acid solution from the bottom of column 17 to a column 23 where most of the solvent and water are taken overhead through line 35. The vapor leaving the top of column 23 through line 35 is fed to a condenser 36 where the vapor is condensed to form a liquid which flows through line 37 to a gravity separator 38. Organic and aqueous layers are formed in the gravity separator and a portion of the organic layer is withdrawn from the gravity separator 38 through a line 24 and is recycled to the solvent extractor 21. The aqueous layer is withdrawn from the gravity separator 38 through a line 25 and is combined with the aqueous phase leaving the extractor 21 through line 27. A part of either the organic phase or the aqueous phase in the gravity separator 38 or part of both phases may be used as reflux in the distillation column 22 (preferably only the organic phase is refluxed). The aqueous liquid combined from streams 25 and 27 is fed through line 28 to a solvent recovery distillation column 29 where solvent is taken overhead and removed through a line 31 to be combined with the solvent recycled through line 39 which leads to the solvent extractor 21. The liquid leaving the bottom of the solvent recovery column 29 through line 30 goes to waste. The bottoms stream 26 from column 23 is fed to a dehydration column 32 where residual water contained in stream 26 is taken overhead and is combined in line 20 with the feed to the solvent extractor 21. The bottom liquid from the dehydration column 32, withdrawn through line 34, contains methacrylic acid and other by-products, but very little solvent or water, and is optionally processed further for separation of methacrylic acid from by-product contaminants such as acetic acid.

The following examples illustrate this invention but those skilled in the art will recognize that many changes can be made in the reaction conditions and solvents without exceeding the scope of this invention.

EXAMPLE 1—FIRST STAGE QUENCH

A gas stream, at a temperature of 285° C., containing, by weight, 6.46% methacrylic acid, 0.63% acetic acid, 8.09% water, 7.97% methacrolein and 76.85% nitrogen was fed to the bottom of a 51 mm diameter, 10 plate glass Oldershaw distillation column at a rate of 15.1 grams per minute. The gas stream was brought into counter-current contact with a recirculating stream of a portion of previously collected condensate which had been cooled to a temperature of 54° C. The feed rate of the liquid fed to top of the column was 180 grams per minute. The gas leaving the top of the column was at atmospheric pressure. The cooling of the gas stream brought about by contact with the cooled, recirculated condensate resulted in condensation of some of the higher-boiling components of the gaseous feed stream. In particular, 55.0% of the methacrylic acid, 47.6% of the acetic acid, 19.9% of the water and 1.9% of the methacrolein contained in the gaseous feed to the Oldershaw column were condensed.

EXAMPLE 2—SECOND STAGE QUENCH

A gaseous stream, at a temperature of 54° C., composed of 3.02 weight percent methacrylic acid, 0.65 weight percent acetic acid, 8.36 weight percent water, 8.27 weight percent methacrolein and 79.70 weight percent nitrogen is fed to the bottom of a 51 mm diameter, 10 plate glass Oldershaw distillation column at a rate of 15.1 grams/minute. A recycle stream of cooled condensate is fed to the top of the Oldershaw column at a rate of 135 grams/minute. The temperature of the recycle stream is 10° C. The gas leaving the top of the column is at atmospheric pressure. At steady-state, the portion of the liquid stream withdrawn from the bottom of the Oldershaw column that is not recycled will contain 98.9% of methacrylic acid, 97.9% of acetic acid, 93.2% of water and 7.6% of methacrolein in the gaseous feed to the Oldershaw column.

EXAMPLE 3

An aqueous stream containing 21.9 weight percent methacrylic acid, 3.5 weight percent acetic acid and 74.6 weight percent water is brought into counter-current contact with an equal weight of a solvent stream containing 1.21 weight percent methacrylic acid, 1.03 weight percent acetic acid, 0.25 weight percent water and 97.51 weight percent n-butyl acetate. The two streams are contacted in such a manner as to be equivalent to an extraction involving six theoretical stages. The extract, which has a composition of 17.83 weight percent methacrylic acid, 2.78 weight percent acetic acid, 4.00 weight percent water and 74.60 weight percent n-butyl acetate is fed to a 51 mm diameter, 20 plate Oldershaw distillation column at a rate of 288 grams/hr. An aqueous stream containing 41.06 weight percent methacrylic acid, 3.82 weight percent acetic acid, and 55.12 weight percent water is fed to the same distillation column at a rate of 486 grams/hr. The column is operated at an overhead pressure of 100 mm Hg, and the temperature at the bottom of the column is maintained at 105° C. The overhead vapor from the distillation column is condensed and allowed to separate into two liquid phases. A portion of the organic phase is returned to the column as reflux. The organic phase has a composition of 0.63 weight percent methacrylic acid, 0.50 weight percent acetic acid, 1.01 weight percent water and 97.86 weight percent n-butyl acetate, and the ratio of reflux to organic distillate was 2.2. None of the aqueous phase, which had a composition of 0.05 weight percent methacrylic acid, 1.20 weight percent acetic acid, 98.24 weight percent water and 0.51 weight percent n-butyl acetate, is used as reflux. The bottoms stream composition was 92.24 weight percent methacrylic acid, 7.69 weight percent acetic acid, 0.06 weight percent water and 0.0091 weight percent n-butyl acetate.

Although this example describes the separation of methacrylic acid from aqueous solution, it is to be understood that the invention also embraces the separation of methacrylic acid from a gaseous mixture and the separation of acrylic acid from either aqueous solution or a gaseous mixture or both.

The following illustrates solvents which can be employed in this invention, and their distribution coefficients and selectivities with methacrylic acid (MAA) and acetate acid (HAc)

| Solvent | Distribution Coefficient[1] | | Selectivity[2] | |
|---|---|---|---|---|
| | MAA | HAC | MAA | HAC |
| Methyl methacrylate | 8.80 | 1.12 | 92.7 | 11.8 |
| Ethyl propionate | 8.48 | 0.78 | 90.5 | 8.36 |
| iso-Butyl acetate | 8.40 | 0.95 | 162.0 | 12.2 |
| n-Propyl acetate | 7.94 | 0.73 | 66.6 | 6.07 |
| n-Butyl acetate | 7.30 | 0.64 | 93.6 | 8.10 |
| iso-Propyl acetate | 6.92 | 0.63 | 66.1 | 4.70 |
| sec-Butyl acetate | 6.84 | 0.63 | 87.5 | 8.00 |
| Methyl isobutyrate | 6.30 | 0.64 | 62.0 | 12.3 |
| Toluene | 4.50 | 0.30 | 373.4 | 24.9 |
| Xylene | 4.50 | 0.26 | 220.8 | 12.8 |

[1]Distribution Coefficient = $\dfrac{\text{wt fraction of component in the extract phase}}{\text{wt fraction of component in the raffinate phase}}$

[2]Selectivity = $\dfrac{\dfrac{\text{wt fraction of component in extract}}{\text{wt fraction of water in extract}}}{\dfrac{\text{wt fraction of component in raffinate}}{\text{wt fraction of water in raffinate}}}$

What is claimed is:

1. A process for separating methacrylic acid from a methacrylic acid-containing gaseous effluent which comprises:
   (a) feeding the gaseous effluent to a first-stage partial condenser wherein the effluent is brought into direct contact with a part of the condensed liquid previously obtained in the condenser, said condenser being at a temperature in the range of from about 16° to 70° C., whereby a portion of the methacrylic acid and water vapor in the effluent are condensed to form a relatively concentrated aqueous methacrylic acid liquid stream and whereby a substantial portion of the methacrylic acid and water vapor leaves the first-stage condenser in the vapor phase along with noncondensible gases and the major portion of methacrolein contained in the effluent;
   (b) feeding the vapor phase, leaving the first-stage condenser, to a second-stage condenser where the vapor is brought into direct contact with a part of the condensed liquid obtained in the second-stage condenser, said second stage condenser being at a temperature equal to or less than that of the first-stage condenser whereby most of the methacrylic acid and a large portion of the water contained in the vapor feed are condensed to form an aqueous methacrylic acid liquid stream that is less concentrated in methacrylic acid than is the liquid leaving the first-stage condenser;
   (c) feeding a liquid stream from the first-stage condenser to a first distillation column where methacrolein is removed as an overhead product;
   (d) feeding a liquid stream from the second-stage condenser to a second distillation column where methacrolein is removed as an overhead product;
   (e) extracting the stream from the bottom of the second distillation column, described in step d, with a suitable solvent to form an organic phase;
   (f) feeding both the organic phase from the extractor and the liquid from the bottom of the first distillation column described in step c, to a third distillation column wherein solvent and water dizeotrope are removed overhead and methacrylic acid is removed from bottom of the column.

2. The process of claim 1 wherein the vapor leaving the second-stage condenser is treated to recover unreacted methacrolein.

3. The process of claim 1 wherein the extraction solvent is selected from a group consisting essentially of n-butyl acetate, iso-butyl acetate, sec-butyl acetate, iso-propyl acetate, n-propyl acetate, toluene, xylene, methyl methacrylate, ethyl proprionate, or methyl isobutyrate.

4. The process of claim 1 wherein the distillation steps are conducted at pressures less than or equal to one atmosphere.

5. A process for separating acrylic acid from an acrylic acid-containing gaseous effluent which comprises:
   (a) feeding the gaseous effluent to a first-stage partial condenser wherein the effluent is brought into direct contact with a part of the condensed liquid previously obtained in the condenser, said condenser being at a temperature in the range of from about 16° to 70° C., whereby a portion of the acrylic acid and water vapor in the effluent are condensed to form a relatively concentrated aqueous acrylic acid stream and whereby a substantial portion of the acrylic acid and water vapor leaves the first-stage condenser in the vapor phase along with non-condensible gases and the major portion of acrolein contained in the reactor effluent;
   (b) feeding the vapor phase, leaving the first-stage condenser, to a second-stage condenser where the vapor is brought into direct contact with a part of the condensed liquid obtained in the second-stage condenser, said second stage condenser being at a temperature equal to or less than that of the first-stage condenser whereby most of the methacrylic acid and a large portion of the water contained in the vapor feed are condensed to form an aqueous acrylic acid solution that is less concentrated in acrylic acid than is the liquid leaving the first-stage condenser;
   (c) feeding a liquid stream from the first-stage condenser to a first distillation column where acrolein is removed as an overhead product;
   (d) feeding a liquid stream from the second-stage condenser to a second distillation column where acrolein is removed as an overhead product;
   (e) extracting the stream from the bottom of the second distillation column, described in step d, with a suitable solvent to form an organic phase;
   (f) feeding both the organic phase from the extractor and the liquid from the bottom of the first distillation column, described in step c, to a third distillation column wherein solvent and water azeotrope are removed overhead and acrylic acid is removed from bottom of the column.

* * * * *

UNITED STATES PATENT AND TRADEMARK OFFICE
CERTIFICATE OF CORRECTION

PATENT NO. : 4,554,054

DATED : November 19, 1985

INVENTOR(S) : ROBERT W. COYLE

It is certified that error appears in the above-identified patent and that said Letters Patent is hereby corrected as shown below:

COLUMN 2, LINE 31 "extract or" should read "extractor"

COLUMN 3, LINES 66, 67 "n-propyl acetate, toluene xylene, methyl methacrylate" should read "n-propyl acetate, toluene, xylene, methyl methacrylate"

COLUMN 8, LINE 48 "methacrylic" should read "acrylic"

Signed and Sealed this

Eighteenth Day of February 1986

[SEAL]

Attest:

DONALD J. QUIGG

Attesting Officer

Commissioner of Patents and Trademarks